United States Patent [19]
Anderson et al.

[11] Patent Number: 5,643,884
[45] Date of Patent: Jul. 1, 1997

[54] LUPANE TRITERPENOID DERIVATIVES

[75] Inventors: Mark Brian Anderson, Orinda; John Henry Musser, San Carlos, both of Calif.

[73] Assignee: Glycomed Incorporated, Alameda, Calif.

[21] Appl. No.: 105,095

[22] Filed: Aug. 9, 1993

[51] Int. Cl.$^6$ .................. A61K 31/705; C07J 17/00
[52] U.S. Cl. .................. 514/26; 514/25; 514/53; 514/61; 514/169; 514/172; 514/176; 514/178; 536/4.1; 536/5; 536/18.7; 536/123.1; 536/123.13
[58] Field of Search .................. 424/1.45, 1.73; 536/5, 6, 18.7; 549/13, 28, 417, 419, 424; 546/195; 514/26, 53, 317, 432

[56] References Cited

U.S. PATENT DOCUMENTS

| | | | |
|---|---|---|---|
| 3,934,027 | 1/1976 | Hess et al. | 424/309 |
| 4,173,648 | 11/1979 | Pifferi et al. | 424/204 |
| 5,356,880 | 10/1994 | Kurono et al. | 514/26 |
| 5,519,008 | 5/1996 | Rao et al. | 514/26 |
| 5,527,890 | 6/1996 | Rao et al. | 536/5 |

OTHER PUBLICATIONS

Juodvirsis et al., CA 72:111711, 1969, "Synthesis of triterpene glycosides", Izr. Sib. Otd. Akad. Nauk. SSSR. (Russian).

Otsuka, H. et al., "Studies on Anti–Inflammatory Agents. V. A New Anti–Inflammatory Constituent of Pyracantha Crenulata ROEM," *Chem. and Pharm. Bulletin*, vol. 29, No. 11, pp. 3099–3104 (1981).

Inada, A. et al., "Phytochemical Studies on Meliaceous Plants. VIII. Structures and Inhibitory Effects on Epstein–Barr Virus Activation of Triterpenoids from Leaves of Chisocheton Macrophyllus KING," *Chem. and Pharm. Bulletin*, vol. 41, No. 3, pp. 617–619 (1993).

Sheth, K. et al., "Tumor Inhibitory Agent from Hyptis Emoryi (Labiatae)," *Journal of Pharm. Sci.*, vol. 61, No. 11, p. 1819 (1972).

Chemical Abstracts, vol. 89, No. 25, Abstract No. 211956 (Kingston, D. et al.) (1978).

Chemical Abstracts, vol. 109, No. 17, Abstract No. 146343 (Tomas–Barberan, F. et al.) (1988).

Chemical Abstracts, vol. 111, No. 25, Abstract No. 228964 (Chen, R. et al.) (1989).

Chemical Abstracts, vol. 110, No. 19, Abstract No. 170211 (Choi, Y.H. et al.) (1989).

Chemical Abstracts, vol. 103, No. 25, Abstract No. 211168 (Fang, X. et al.) (1985).

Miles, D.H. et al., "Tumor Inhibitors I: Preliminary Investigation of Antitumor Activity of Sarracenia Flava," *Journal of Pharm. Sci.*, vol. 63, No. 4, pp. 613–615 (1974).

Supplementary European Search Report issued May 31, 1996.

B.N. Rao et al., Siayl Lewis X Mimics Derived from a Pharmacophore Search Are Selectin Inhibitors with Anti–Inflammatory Activity, *J. of Biol. Chem.*, vol. 269, No. 31, pp. 19663–19666 (1994).

Otsuka, et al., "Studies on Anti–inflammatory Agents. V.[1] A New Anti–inflammatory Constituent of *Pyracantha crenulata Roem* [2]", Chem.Pharm.Bull. 29:11:3099–3104 (1981).

(List continued on next page.)

Primary Examiner—Gary E. Hollinden
Assistant Examiner—Lara E. Chapman
Attorney, Agent, or Firm—Lyon & Lyon

[57] ABSTRACT

This invention relates generally to the field of medicinal chemistry, and more specifically to derivatives of a subclass of triterpenoid acids that have multi-medicament properties, that is derivatives of the lupane, betulinic acid, formulations containing such, and their use to prevent or treat certain diseases, and preferably to derivatives or analogues of betulinic acid, that have the following structural formula (1):

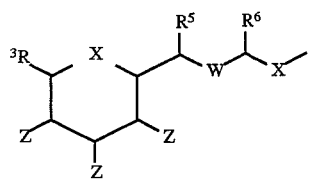

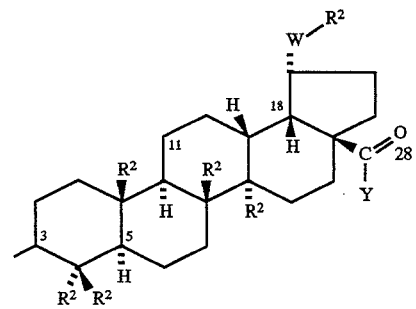

wherein:

Y is $OR^1$, $NR^1_2$, $O^-M^1$;

$R^1$ is H, LOWER ALKYL, $M^1$ is $Na^+$, $K^+$, $Mg^{++}$, $Ca^{++}$ ions;

each $R^2$ is independently $CH_2OR_1$ or $CH_3$;

each $R^3$ is independently H, $CH_3$, lower alkyl, COY, $CH_2OH$, $CH_2OCH_2CH=CH_2$, $CH_2OSO_3^-M^1$;

each Z is independently $NHR^1_2$, $NR^1Ac$, $NR^1Bz$, H, $OCH_3$, lower alkyl, OH, $OSO_3^-M^1$, $OCH_2CH=CH_2$, $OCH_2CO_2H$ or O-glucoside;

each X is independently O, S, $NR^1$ or $NR_2^1$ each W is independently C=O, $C=CR^1_2$, $CR^1CR^1_3$, $CR^1-CR^1_2OR^1$, $COR^1-CR^1OR^1$, $COR^1CR^1_2OR^1$, $CR^1CR^1_2NR^1_2$, $CR^1CR^1_2OCR^1COY$, $CHR^4$;

$R^4$ is H, OH, $OSO_3^-M^1$, or $NH(CH_2)nNH_2$, where n=1–8, or $NH-Ph-NH_2$ where Ph=an phenyl or naphthyl rings substituted with up to 3 amine functionalities and the remaining substitutions can be H, $R^1$, $R^2$ or COY;

$R^5$ and $R^6$ are independently H, $CH_3$, or taken together form a 5 or 6 membered carbocyclic ring.

19 Claims, 4 Drawing Sheets

OTHER PUBLICATIONS

Yasukawa, et al., "Sterol and Triterpene Derivatives from Plants Inhibit the Effects of a Tumor Promoter, and Sitosterol and Betulinic Acid Inhibit Tumor Formation in Mouse Skin Two–Stage Carcinogenesis," Oncology 48:72–76 (1991).

Heby, "Ornithine Decarboxylase as Target of Chemotherapy," Adv.Enzyme Regul., 24:103–124 (1985).

Choi, et al., "Ellagic Acid Derivatives of Agrostistachys hookeri[1]," Planta Medica, pp. 511–513 (1988).

CA 86:68400, 1976, Hiller et al., "Isolation of betulic acid 3–0.beta.–d–glcoside", a saponin from Eryngium bromelififolium Delar., (German) 1976.

FIG. 1.
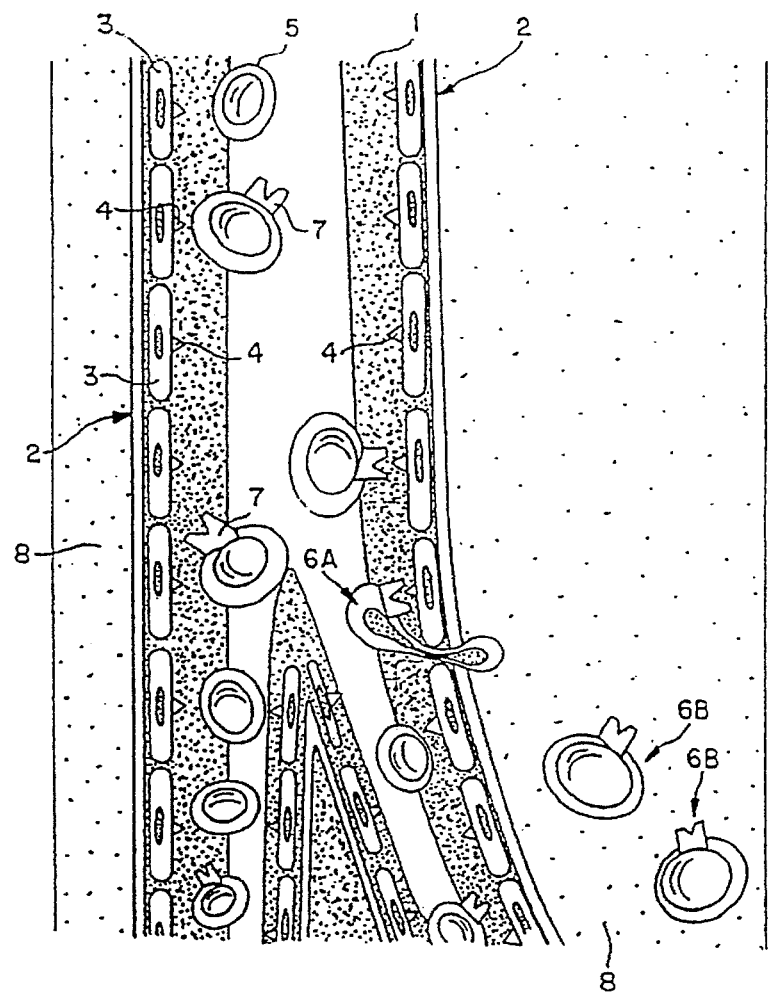
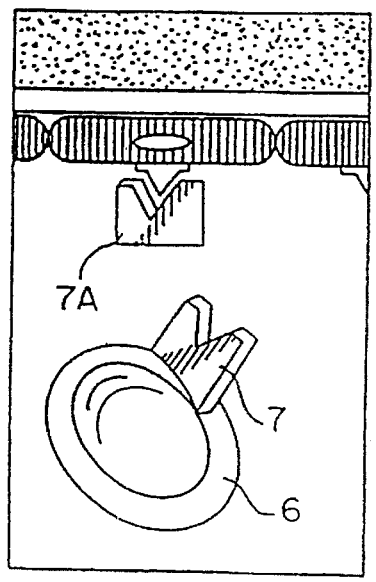
FIG. 2.

LUPANE TRITERPENOID DERIVATIVES

FIELD OF THE INVENTION

This invention relates generally to the field of medicinal chemistry. More specifically, to derivatives of a subclass of triterpenoid acids that have multi-medicament properties, that is derivatives of the lupanes, formulations containing such, and their use to prevent or treat certain diseases.

BACKGROUND OF THE INVENTION

Triterpenoids comprise a class of natural products that are reported to have medicament properties including anti-ulcer, anti-inflammatory, anti-allergy, anti-hepatitis and antiviral activities. As shown below, some examples of this class of molecules exhibit a ring structure having either 5 six membered rings, or 4 six membered rings and one five membered ring. Members of this latter classification are termed lupanes.

Perhaps one of the most studied of the triterpenoids is glycyrrhetinic acid, shown below, and derivatives thereof. For instance, certain glycyrrhetinic acid derivatives can prevent or heal gastric ulcers. Doll, R. et al., *Lancet* 11: 793 (1962). Among such compounds known in the art are carbenoxolone (U.S. Pat. No. 3,070,623), glycyrrhetinic acid ester derivatives having substituents at the 3-O position (U.S. Pat. No. 3,070,624), amino acid salts of glycyrrhetinic acid (Japanese Patent Publication JP-A-44-32798), amide derivatives of glycyrrhetinic acid (Belgian Patent No. 753773), amide derivatives of 11-deoxoglycyrrhetinic acid (British Patent No. 1346871), cicloxolone (*Journal of Antimicrobial Chemotherapy*, 18:B: 1845-200(1986), and glycyrrhizic acid and its derivatives (*Chem. Pharm. Bull.* 39(1): 112–115), (1991).

Additionally, U.S. Pat. No. 3,934,027 shows 18-β-glycyrrhetinic acid amides that are useful as antiulcer agents. U.S. Pat. No. 4,173,648 shows 3-β-hydroxy-18-β-olean-9-en-3O-oic acids also for treating ulcers.

Finally, WO 93/09129 describes certain triterpene compounds that exhibit anti-inflammatory activity.

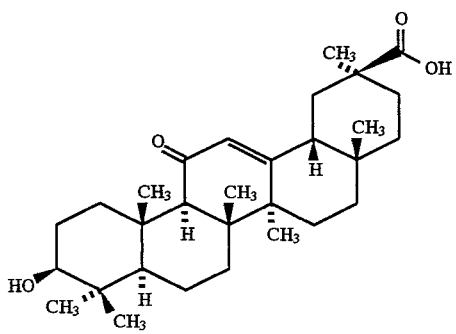

Glycyrrhetinic acid

Triterpenoids that exhibit a ring structure having 4 six membered rings and one five membered ring, are termed lupanes. Betulinic acid, a member of this class of natural products, has the following structure:

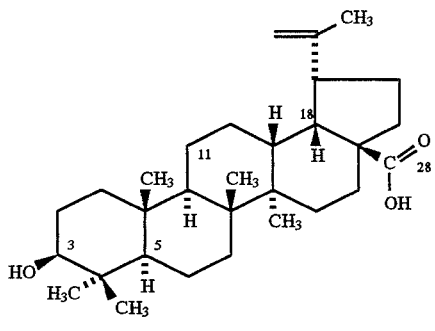

Betulinic acid

Similar to other triterpenoids, betulinic acid is known to have certain medical applications, including use as an anti-cancer drug. See, for example, JP 87,301,580. Anti-cancer applications are premised on the observation that cells require an adequate level of polyamines to grow at an optimal rate, and that cell growth can be inhibited by drugs that interfere with the enzymatic synthesis of polyamines. Four enzymes are known to be involved in the synthesis of polyamines: ornithine decarboxylase, S-adenosylmethionine decarboxylase, spermidine synthase and spermine synthase. Heby, O., Adv. Enzyme Regul., 24: 103–124, (1985). The activities of the two decarboxylases are rate limiting, and betulinic acid is a known inhibitor of ornithine decarboxylase. Yasukawa, K. et al. *Oncology* 48: 72–76 (1991). Its capacity to inhibit ornithine decarboxylase is, at least in part, responsible for its anti-cancer activity.

Although there have been some studies on the derivization of triterpenoids, particularly as related to glycyrrhetinic acid, as discussed above, little work has been done describing derivatives of betulinic acid. Choi et al have shown that betulinic acid 3-monoacetate, and betulinic acid methyl ester exhibit $ED_{50}$ values of 10.5 and 6.8 ug/ml, respectively, against P-388 lymphocytic leukemia cells. Choi, Y-H et al., Planta Medica vol. XLVII, pages 511–513, (1988).

It will be appreciated that because of the medicament properties of betulinic acid, it would be desirable to identify regions of the molecule that could be chemically modified in order to synthesis analogues or derivatives that are active against a wider spectrum of cancers, or that can be used to treat diseases other than cancer.

The lupanes, and specifically betulinic acid, have been reported to be effective anti-inflammatory agents. The anti-inflammatory activity of betulinic acid is, at least in part, due to its capacity to inhibit enzymes involved in leukotriene biosynthesis, including 5-lipoxygenase. Sotomatsu, S., et al., *Skin and Urology* 21: 138 (1959) and Inoue, H., et al., *Chem. Pharm. Bull.* 2: 897–901 (1986). Thus, a further reason to identify new betulinic acid derivatives is to take advantage of betulinic acids multi-medicament properties, and to produce medicaments that can be used to treat different diseases.

SUMMARY OF THE INVENTION

A first object of the invention is a description of triterpenoids, and preferably derivatives or analogues of the lupanes.

A second object of the invention is a description of derivatives or analogues of the lupane, betulinic acid, that have multi-medicament properties, including inhibition of ornithine decarboxylase, inhibition of certain enzymes involved in leukotriene biosynthesis, including 5-lipoxygenase, and the hithertofore unknown property of binding to certain selectins.

A third object of the invention is a description of preferred derivatives or analogues of the triterpenoid, betulinic acid, consisting of preferred modifications at the 3 position of betulinic acid on the E ring of the triterpenoid core structure, such modifications consisting of binding a glucoside, directly or indirectly thereto, thus increasing their medicament properties.

A fourth object of the invention is the description of derivatives or analogues of betulinic acid, that have the following structural formula (1):

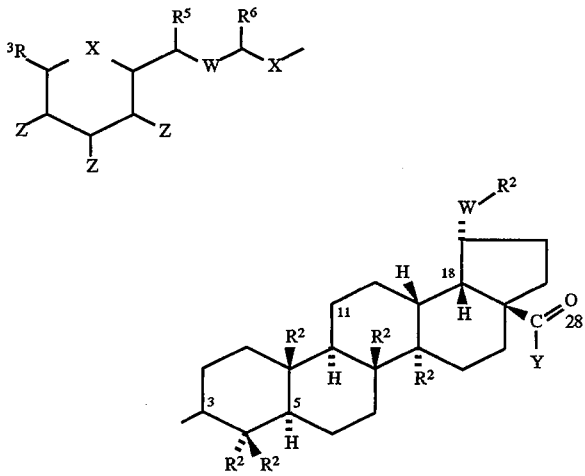

wherein:

Y is $OR^1$, $NR^1_2$, $O^-M^1$;

$R^1$ is H, LOWER ALKYL, $M^1$ is $Na^+$, $K^+$, $Mg^{++}$, $Ca^{++}$ ions;

each $R^2$ is independently $CH_2OR_1$ or $CH_3$;

each $R^3$ is independently H, $CH_3$, lower alkyl, COY, $CH_2OH$, $CH_2OCH_2CH=CH_2$, $CH_2OSO_3^-M^1$;

each Z is independently $NHR^1_2$, $NR^1Ac$, $NR^1Bz$, H, $OCH_3$, lower alkyl, OH, $OSO_3^-M^1$, $OCH_2CH=CH_2$, $OCH_2CO_2H$ or O-glucoside;

each X is independently O, S, $NR^1$ or $NR_2^1$ each W is independently C=O, C=$CR^1_2$, $CR^1CR^1_3$, $CR^1$-$CR^1_2OR^1$, $COR^1$-$CR^1OR^1$, $COR^1CR^1_2OR^1$, $CR^1CR^1_2NR^1_2$, $CR^1CR^1_2OCR^1COY$, $CHR^4$;

$R^4$ is H, OH, $OSO_3^-M^1$, or $NH(CH_2)nNH_2$, where n=1–8, or $NH-Ph-NH_2$ where Ph=an phenyl or naphthyl rings substituted with up to 3 amine functionalities and the remaining substitutions can be H, $R^1$, $R^2$ or COY;

$R^5$ and $R^6$ are independently H, $CH_3$, or taken together form a 5 or 6 membered carbocyclic ring.

A fifth object of the invention is to provide a pharmaceutical formulation containing the compound of formula (1).

A sixth object of the invention is a description of methods to treat or prevent disease by administering an effective amount of the aforementioned derivatives or analogues of betulinic acid, which diseases include cancer, autoimmunity, (i.e., arthritis), and the inflammatory response.

A seventh object of the invention is a description of methods to image sites of disease by administering labeled derivatives or analogues of betulinic acid of structural formula (1) and locating the labeled derivatives at a disease site in the body.

These and other objects, advantages and features of the present invention will become apparent to those persons skilled in the art upon reading the details of the isolation, structure, formulation and usage of the invention compounds as more fully set forth below.

BRIEF DESCRIPTION OF THE DRAWINGS

This invention may be better understood and its numerous objects, advantages and features will become apparent to those skilled in the art by reference to the accompanying drawings as follows:

FIG. 1 is a cross-sectional schematic view showing the interaction between white blood cells and activated endothelial cells; and FIG. 2 is a cross-sectional schematic view showing how compounds of the invention may act as selectin ligands and thus be used as pharmaceuticals to block E-selectin.

DETAILED DESCRIPTION OF PREFERRED EMBODIMENTS

Figure 3:
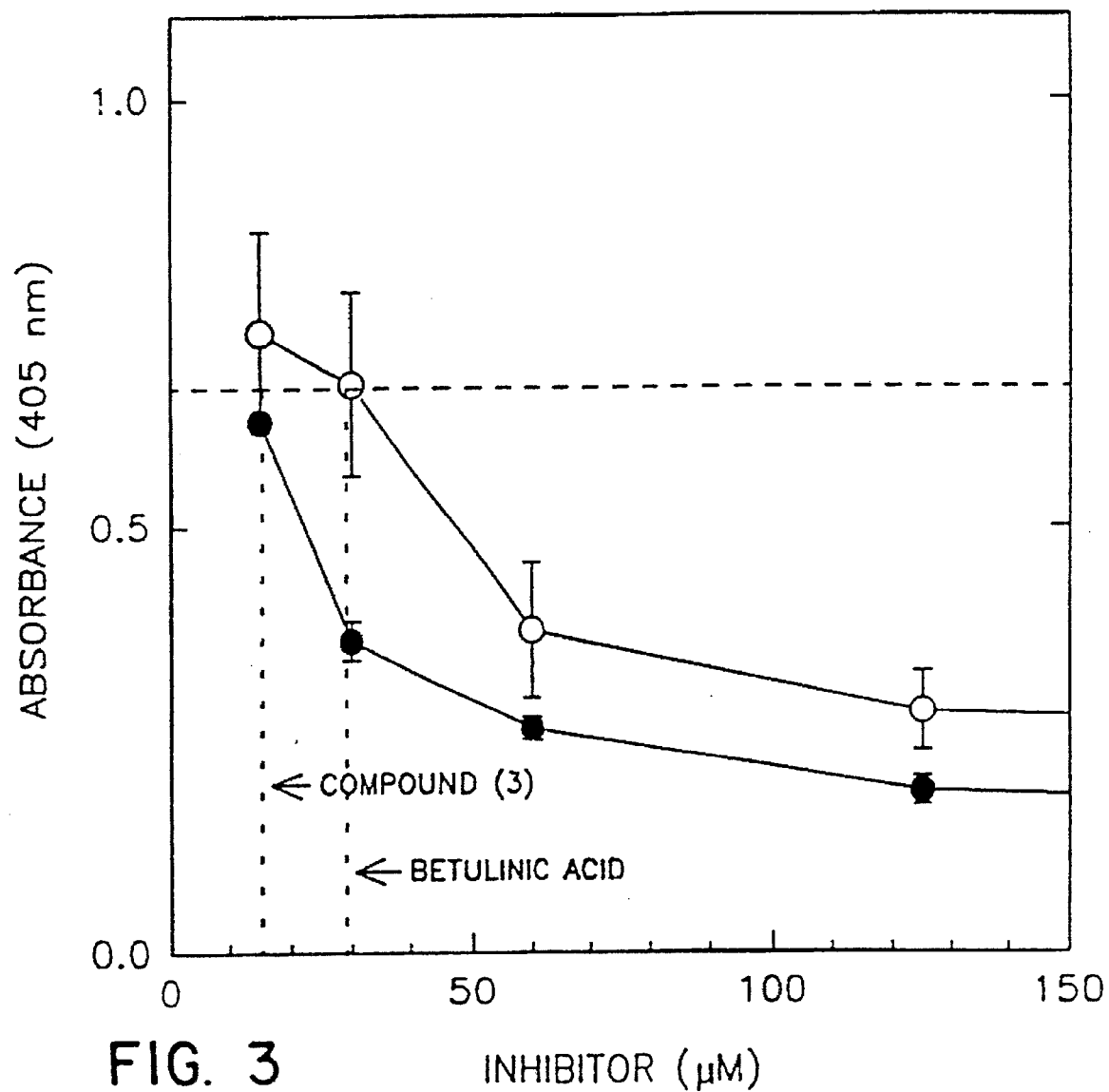
FIG. 3 shows the inhibition of cancer cell adhesion to E-selectin by compound (3) and betulinic acid.

Before the present compounds and compositions, and processes for isolating and using such are described, it is to be understood that this invention is not limited to the particular compositions, methods or processes described as such and may, of course, vary as would be known by the skilled practitioner of this art. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a ligand" includes mixtures of compounds, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

Glucoside is defined to include glucose, fucose, galactose, mannose, neutral or charged sugars, arabinose, xylose and chemically related sugars.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. All publications mentioned herein are incorporated herein by reference.

Some standard abbreviations used in connection with the present invention include: BSA, bovine serum albumin; DEAE, diethylaminoethyl; DMSO, dimethylsulfoxide; ELAM-1, endothelial/leukocyte adhesion molecule-1; HPTLC, high performance thin layer chromatography;

LECAM-1, leukocyte/endothelial cell adhesion molecule-1; MOPS, 3-[N-Morpholino]propanesulfonic acid; NANA, N-acetylneuraminic acid; PVC, polyvinylchloride; TLC, thin layer chromatography; TFA, trifluoroacetic acid; Tris, tris (hydroxymethyl) aminomethane.

General Overview

Here and throughout the description of the invention, different stereo-configurations of the invention compounds are not shown but are understood to be encompassed by this disclosure and the appended claims.

One use of the compounds of the instant invention is to treat diseases that have, as one component of the disease, unwanted cell-cell adhesion. Numerous such diseases are well known to the skilled practitioner of this art and include unwanted inflammation, tumor metastasis, autoimmune diseases and others. FIGS. 1 and 2 pictorially present the application of the invention compounds in the inflammatory context.

FIG. 1, a cross-sectional view of a blood vessel 1. The vessel wall 2 is lined internally with endothelial cells 3. The endothelial cells 3 can be activated causing the cells 3 to synthesize ELAM-1 which is displayed as a triangular surface receptor 4. Both red blood cells 5 and white blood cells 6 flow in the vessel 1. The white blood cells 6 display carbohydrate compounds 7 which have chemical and physical characteristics which allow the compounds 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as unwanted inflammation.

Referring now to FIG. 2, the inventors have produced compounds 7 apart from their presence on the surface of white blood cells 6. These isolated compounds 7A adhere to ELAM-1 by themselves and can be formulated into pharmaceutical compositions, which when administered will effectively block the ELAM-1 and prevent the adhesion of a receptor 7 connected to a white blood cell 6. By administering pharmaceutically effective amounts of compounds 7A, some, but not all, of the white blood cells will not reach the surrounding tissue. By slowing the rate at which the white blood cells reach the surrounding tissue, inflammation can be prevented and/or alleviated.

It is known that for an acute inflammatory response to occur, circulating neutrophils must bind to and penetrate the vascular wall and access the site of injury. Several molecules have been implicated in this interaction, including a family of putative carbohydrate compounds and their receptors. One molecule which has been previously isolated and identified is the endogenous carbohydrate ligand for endothelial leukocyte adhesion molecule-1 (hereinafter ELAM-1) and the ligand for LECAM-1. Surprisingly, one of the properties of the compounds of the invention is that they are selectin ligands. The present invention involves the characterization of the selectin ligand properties of the compounds shown in structural formula 1.

For certain cancers to spread throughout a patients body, a process termed metastasis, cell-cell adhesion must take place. Specifically, cancer cells must migrate from their site of origin and gain access to a blood vessel to facilitate colonization at distant sites. A critical aspect of this process is adhesion of cancer cells to endothelial cells that line the blood vessel wall, a step prior to migrating into surrounding tissue. This process can be interrupted by the administration of compounds of the invention which generally aid in blocking cell-cell adhesion. Accordingly, compounds of the invention can be used to retard the spread of cancer cells which display receptors which adhere to a compound of formula I.

Triterpenoid Acid Derivatives—Assays for Biological Activity

Derivatives of betulinic acids encompassed by general structural formula I can be tested for biological activities in accordance with certain assay procedures as will now be described.

Leukotriene Biosynthesis

Several assays can be performed to assess the inhibitory activity of the invention compounds against enzymes involved in leukotriene biosynthesis. For instance, leukotriene biosynthesis from arachidonic acid commences with 5-lipoxygenase oxidation of arachidonic acid to form 5-hydroperoxyeicosatetraenoic acid (5-HPETE), and in turn, leukotriene A4 and 5-hydroxyeicosatetraenoic acid (5-HETE). Assays for 5-lipoxygenase are known in the art and can be readily performed as described by Shimuzu, T., et al., *Proc. Natl. Acad. Sci. USA* 81: 693–698 (1984); and Epan, R., et al., *J. Biol. Chem.* 260: 11554–11559 (1985).

5-Lipoxygenase catalyzes the oxidative metabolism of arachidonic acid to 5-hydroxyperoxyeicosatetranoic acid (5-HPETE), the initial reaction leading to the formation of certain leukotrienes. Thus, compounds that inhibit 5-lipoxygenase will have significant medical applications that require regulating or lowering leukotriene levels. Thus, the compounds of the instant invention are assayed for their capacity to inhibit 5-lipoxygenase using a crude enzyme preparation from rat basophilic leukemia cells (RBL-1) (Shimuzu, T., Radmark, O. and Samuelsson, B. *Proc. Natl. Acad. Sci. USA* 81: 698–693 (1984) and Egan, R. W. and Gale, P. H. *J. Biol. Chem.* 260: 11554–11559 (1985)).

Anti-Inflammatory Activity

The arachidonic acid (AA), murine skin inflammation model, described by Harris, R. R. et al. (*Skin Pharmacol* 3: 29–40 (1990)) may be used to test the anti-inflammatory activity of the invention compounds relative to betulinic acid. Arachidonic acid is known to induce an inflammatory response and the compounds were tested for their capacity to inhibit the response.

Briefly, the compounds at an appropriate concentration are dissolved in a suitable solvent, and applied to a rodent ear immediately following application of arachidonic acid (AA). A control of AA alone is run. About 90 minutes later a 6 mm disk of each ear is removed and weighed. The percent inhibition of swelling caused by AA alone is calculated for the betulinic acid derivatives of the invention and compared to betulinic acid.

Anti-metastatic Activity

Certain cancer cells are known to adhere to E-selectin via E-selectin ligands on their cell surface, and this event is one component of the metastatic process. Thus, the anti-metastatic activity of the betulinic acid derivatives of the instant invention may be determined by assaying their capacity to prevent cancer cell adhesion to E-selectin. The assay generally consists of combining the appropriate test compound, an E-Selectin chimera which contains an IgG tail, a detection system consisting of biotinylated anti-human Ig (Fc specific), and streptavidin-alkaline phosphatase all in a suitable reaction solution. The mixture is rotated briskly on a rotary platform at room temperature for about 30–60 minutes. Particulate matter is removed by centrifugation, and the soluble fraction is transferred onto 96-well microtiter plates containing glutaraldehyde fixed LS174T colon carcinoma cells. This cell line is known to adhere to E-selectin. After 60 minutes at 37° C., plates are washed and E-selectin chimera bound to cells is quantified by addition of pNPP substrate in 1M diethanolamine buffer containing 0.1 mg/ml $MgCl_2$ at pH 9.8. Plates are developed in the dark and read at 405 nm. The $IC_{50}$ values are calculated and are the lowest concentrations from serial two-fold dilutions (quadruplicate wells at each concentration) which inhibits cell binding by 50% or more relative to the control.

Selectin Binding Assays

Such assays can take several formats including cell based assays that employ cells which express the desired cell surface selectin receptor. Foxall, C. et al., *Journal of Cell Biology* 117: 895–902 (1992). The cells are used as probes to screen compounds by determining if the compounds adhere to the cells under assay conditions known to those skilled in the art. Alternatively, Elisa based assays can be utilized to identify invention compounds that bind to a chosen selectin. Such assays are described by S. R. Watson, C. Fennie, and L. A. Lasky, *Nature* 349: 164–167, (1991); S. R. Watson, Y. Imai, C. Fennie, J. Geoffrey, M. Singer, S. D. Rosen, L. A. Lasky, *J. Cell Biol.* 115: 235–243; (1991) or S. R. Watson, Y. Imai, C. Fennie, J. S. Geoffrey, S. D. Rosen, L. A. Lasky, *Journal of Cell Biology*, 110: 2221–2229, (1991) and Foxall, C. et al., *Journal of Cell Biology*, 117: 895–902 (1992).

Conjugates

It should be pointed out that various "linker" groups can be attached to the betulinic acid derivatives of the present invention and the linker groups can be used to attach various additional compounds such as pharmaceutically acceptable drugs. By using the linker various conjugates are formed i.e. ligand-linker-drug conjugates are formed which provide effective drug delivery systems for the drug which is linked to the ligand compound of the invention. It is especially preferred to attach a drug with anti-inflammatory characteristics in that the ligand binds to ELAM-1 which is associated with inflammation. Accordingly, non-steroidal anti-inflammatory drugs (NSAIDs) such as naproxen or ibuprofen which act as anti-inflammatory agents could be administered bound to the ligand and could be administered systemically in smaller amounts than usual while obtaining an equivalent effect or even greater anti-inflammatory effect at the site of inflammation. The drug could be attached by an enzymatically cleavable linker cleaved by an enzyme such as an esterase. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation, without adverse side effects. Other drug delivery systems may be polymeric backbones which may be, but are not limited to, simple polymers, polymeric carbohydrates, cyclodextrins, heparin or its derivatives, peptides, polymeric beads, etc.

Use and Administration

The betulinic acid derivatives of the invention can be administered to a subject in need thereof to treat the subject by either prophylactically preventing inflammation or relieving it after it has begun. The compounds are preferably administered with a pharmaceutically acceptable carrier, the nature of the carrier differing with the mode of administration, for example, oral administration, usually using a solid carrier and I.V. administration of a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation.

A sufficient amount of ligand molecules should be administered to bind to a substantial portion of the ELAM-1 expected to cause or actually causing inflammation so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose of compounds to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of the compounds administered as blocking agents must be adjusted carefully based on the particular needs of the patient while taking into consideration a variety of factors such as the type of disease that is being treated.

It is believed that the compounds or blocking agents of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot formed has often suffered damage. When the antithrombotic has removed the clot, the damaged tissue beneath the clot and other damaged tissue in the endothelial lining which has been deprived of oxygen, become activated. The activated endothelial cells then synthesize the ELAM-1 receptors within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The compounds of structural formula I can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the ligand molecules adequate to achieve the desired state in the subject being treated.

The various compounds of the present invention can be used by themselves or in combination with pharmaceutically acceptable excipient materials as described above. However, the compounds of the invention can be made as conjugates wherein the compounds of the invention are linked in some manner to a label. By forming such conjugates, the ligand compounds of the invention act as biochemical delivery systems for the label so that a site of inflammation can be detected.

The ligand molecules of the invention could also be used as laboratory probes to test for the presence of a selectin receptor in a sample. Such probes are preferably labeled such as with a radioactive, fluorescent or enzyme activated label.

SYNTHETIC STRATEGY

Throughout this discussion, a standard numbering scheme for the triterpene nucleus will be referred to as described in the Merck Index for betulin (The Merck Index 11: 1212, (1989).

Synthesis of certain of the betulinic acid compounds of the invention requires manipulation about the 3-position of the triterpene nucleus. Some of these manipulations involve a double inversion methodology about this center.

The compound can be inverted from the β- to the α- form i.e. the $C_3$-β-OH to the $C_3$-α-OH using the Mitsunobu method (Mitsunobu, O. *Synthesis* (1981), 1) followed by use of the carbon glycosidation procedures described herein.

Other manipulations can be performed on, but not limited to, the C28 carboxylic acid such as, monovalent or polyvalent attachment to amine functionalities of a drug, linker or polymeric backbone; reduction of the carboxylic acid to the alcohol using standard conditions with subsequent manipulation of the resultant alcohol such as, replacement of the alcohol functionality for a halide, amine, sulfide or other general functional group using standard conditions; oxidation of the resultant alcohol to the aldehyde which can be further functionalized such as, reductive amination to amines, polyamines, polymer supported amines or Wittig methodologies; and glycosidations of the resultant alcohol or carbono-glycosidation conditions as shown in this document or amines with mono-, di-, tri- or oligosaccharides. In general, standard methodologies may be used to transform the C28 carboxylic acid group to other useful functionalities or derivatives.

In some instances, a benzyl ester protecting group can be used for the protection of the E-ring carboxyl group. Subsequent removal will also provide reduction of the C20–29 olefin function to afford C19 isopropyl betulinic acid conjugates.

Other manipulations can be performed on, but not limited to, the C19 exocyclic olefin (that is the C20–29 olefin) in which the olefin can be converted under standard conditions such as, osmium tetroxide methodologies, to a diol which can be subsequently oxidized to the C20 ketone using standard conditions with sodium periodate in methanol. Other manipulations can include diol formation with subsequent glycosidation with mono-, di-, tri- or oligosaccharides. The olefin can be reacted with a variety of hydroborating agents under standard conditions for the formation of a terminal alcohol which can be oxidized to an aldehyde or carboxylic acid for the introduction of other functional groups under standard conditions. The resultant C20 ketone can be reduced to the R or S alcohol configuration using alpine borane conditions (see: Aldrichimica Acta 15(3), 68 (1982)); treated with Wittig or stabilized Wittig reagents under standard conditions for the placement of other desired functional groups; reductive aminations or reduction with subsequent glycosidation or carbon-glycosidation under standard conditions or carbon-glycosidation conditions as shown in this document.

Other Synthetic Aspects

The synthesis of other compounds containing alternate carbohydrates attached to the carbon linking arms for the glycoside conjugates are accomplished by usual glycosidation methods. Alternately, any carbohydrate unit being charged or uncharged and/or desoxygenated species can be formed using the carbon-glycosidation procedure given in this disclosure, but this disclosure does not exclude the analogs prepared from branched, linear or other forms of di-, tri- and poly saccharides or oligosaccharides or combinations. The derivatized carbon-glycoside can be further utilized as a linking group between a pyran ring and the spacer attached to the betulinic acid nucleus by a selective protection methodology involving use of a 2'3'-benzylidene derivative (see Example 4) in which selective rearrangement and/or functionalization and/or glycosidation can be accomplished prior to deprotection. Thus, the various derivatives are converted to potentially more useful compounds.

Multivalent Forms of the Receptor Binding Compounds

The affinity of the compounds of the invention for a receptor can be enhanced by providing multiple copies of the ligand in close proximity, preferably using a scaffolding provided by a carrier moiety. It has been shown that provision of such multiple valence with optimal spacing between the moieties dramatically improves binding to a receptor. (See, for example, Lee, Y. C. et al., *Biochem* 23: 4255 (1984)).

The multivalency and spacing can be controlled by selection of a suitable carrier moiety. Such moieties include but are not limited to molecular supports which contain a multiplicity of functional groups that can be reacted with functional groups associated with the compounds of the invention. A particularly preferred approach involves coupling of the compounds of the invention to amino groups of the carrier through reductive amination. Reductive amination is a particularly convenient way to couple aldehyde moieties to free amino groups by first forming the Schiff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and a reducing agent is added at high pH to complete the reaction.

Particularly convenient carrier moieties to obtain multivalent forms of the invention compounds include (amines (e.g. $N(CH_2CH_2NH_2)_3$), proteins and peptides, particularly those containing lysyl residues which have ω-amino groups available for binding. It is also useful to include in the peptide or protein at least one tyrosine residue, as this offers a convenient site for labeling, for example with radioactive iodine. A particularly convenient carrier to obtain a trivalent couple is the peptide Lys-Tyr-Lys. Complete reaction of the compounds of the invention with the free amino groups on this peptide result in a trivalent moiety. Thus, compounds of the invention of the general formula (I) may be used to make multivalent constructs:

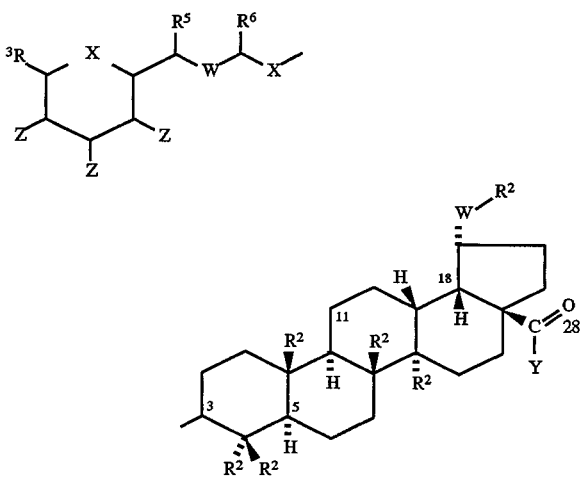

Attachments of the ligand to the amine, or vice versa, by reductive amination would produce multivalent compounds. Preferred attachment points would be at the C28 carbonyl at Y, R3, R4, R5, R6, and W, and particularly at positions C28 carbonyl, R3, R5, R6 and W.

Of course, a variety of carriers can be used, including proteins such as BSA or HSA, a multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the carbohydrate compounds of the invention may be oxidized to contain carboxyl groups which can then be derivatized with either free amino groups to form amides or with hydroxyl groups to form esters. In addition, a suitably functionalized biotin tether may be attached with subsequent complexation with avidin for mulitvalent forms.

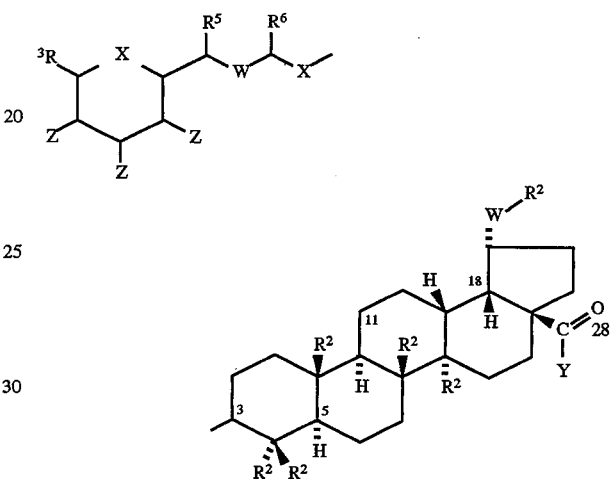

The structure of formula (I) above may be in different isomeric forms and such are encompassed by this disclosure. In particular, the carbon glycoside moiety may be in either the alpha or beta configuration and the linkage by which any sugar is attached at the A-Ring C-3 position may be either axial or equatorial. For instance, acetates and benzoates may serve as protecting groups for the hydroxyl groups in sugars and display neighboring group participation in glycosidation reactions. Thus, by judicious choice of protecting groups prior to the glycosidation, i.e., benzyl ethers, acetates or benzoates, one can preferentially select for either the alpha- or beta- carbon linked glycosides (H. Paulsen, Angew *Chem. Int. Ed. Engl.*, 21: 155 (1982); R. R. Schmidt, "Synthesis of Carbon linked glycosides in Comprehensive Organic Synthesis", Ed. B. M. Trost, 6:33–64). Thus, here and throughout the different stereo configurations are not shown but are understood to be encompassed by this disclosure and the appended claims.

EXAMPLES

The following examples are put forth so as to provide those of ordinary skill in the art with a complete disclosure and description of how to make the compounds and compositions of the invention and are not intended to limit the scope of what the inventors regard as their invention. Efforts have been made to ensure accuracy with respect to numbers that would be used (e.g., amounts, temperature, etc.) but some experimental errors and deviations should be accounted for. Unless indicated otherwise, parts are parts by weight, molecular weight is weight average molecular weight, temperature is in degrees centigrade and pressure is at or near atmospheric.

General

Reagents were purchased from commercial suppliers such as Aldrich Chemical Company or Lancaster Synthesis Ltd.

and were used without further purification unless otherwise indicated. Tetrahydrofuran (THF) and dimethylforamide (DMF) were purchased from Aldrich in sure seal bottles and used as received. All solvents were purified by using normal methods unless otherwise indicated. Reactions were done under a positive pressure of nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried prior to use. Analytical thin layer chromatography (tlc) was performed on glass-backed silica gel 60 F 254 plates (Analtech, 0.25 mm) and eluted with the appropiate solvent ratios (v/v) and are denoted where appropiate. The reactions were assayed by tlc and terminated as judged by the consumption of starting material.

Visualization of the tlc plates was done with a p-anisaldehyde spray reagent or phosphomolybdic acid reagent (Aldrich Chemical 20% wt in ethanol) and activated with heat.

Work-ups were typically done by doubling the reaction volume with the reaction solvent or extraction solvent and then washing with the indicated aqueous solutions using 25% by volume of the extraction volume unless otherwise indicated.

Product solutions were dried over $Na_2SO_4$ prior to filtration and evaporation of the solvents under reduced pressure on a rotary evaporator and noted as solvents removed in vacuo.

Plug filtration refers to using a weight ratio of 10:1 of silica gel to crude product and eluting with a solvent to remove salts and baseline impurities.

Flash column chromatography (Still, W. C.; Kahn, M.; Mitra, A. J. Org. Chem., 43: 2923, (1978) was performed using Baker grade flash silica gel (47–61 mm) and a weight ratio of 20–50 to 1 unless otherwise stated.

$^1$H-NMR spectra were recorded on a Varian 300 instrument operating at 300 MHz and $^{13}$C-NMR spectra were recorded on a Varian 300 instrument operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or as a mixed NMR solvent mixture when necessary, or internally tetramethylsilane (0.00 ppm) when appropiate.

For Peak multiplicities, the following abbreviations are used: s (singlet), d (doublet), t (triplet), m (multiplet), br (broadened), dd (doublet of doublets), dt (doublet of triplets). Coupling constants, in Hertz.

Infrared spectra were recorded on a Perkin-Elmer FT-IR spectrometer as neat oils, or as $CDCl_3$ solutions, and are reported in wave numbers ($cm^{-1}$). The mass spectra were obtained using FAB.

The yields indicated are yields of isolated products purified by flash chromatography and having a purity of greater than 95% as indicated by TLC and 300 MHz $^1$H-NMR.

Example 1

Preparation of 2-Chloromethyl-3-(tri-O-benzyl-α-L-C-fucopyranoside)-1-propene (1)

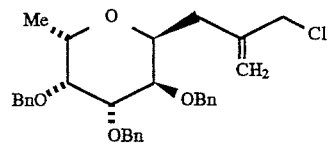

To a solution of tri-O-benzyl-L-fucopyranose (20.0 g, 46.03 mmole, 1.00 mmole equiv.) in anhydrous acetonitrile (200 mL) at 0° C. was added 2-chloromethyl-3-trimethylsilyl-1-propene (30.0 g, 184.34 mmole, 4.00 mmole equiv.). Trimethylsilane trifluoromethane sulfonic acid (10.24 g, 46.03 mmol, 1.00 mmole equiv.) was added dropwise in anhydrous acetonitrile (30 mL, overall reaction concentration 0.2M) and the reaction contents stirred at 0° C. for 30 minutes. After 30 minutes, the reaction was diluted with ethyl acetate (230 mL) and the reaction was terminated by pouring the contents slowly into aqueous saturated sodium bicarbonate. The heterogeneous layers were separated and the organic phase was washed twice with portions of water, 1.0M hydrochloric acid and brine. The crude product was dried over anhydrous sodium sulfate, filtered and plugged through a small pad of silica gel. The solvent was removed in vacuo which afforded an oil that was chromatographed on Baker grade flash silica gel (47–61 mm) (ratio of 50 to 1) and eluted with 5 or 10% ethyl acetate in hexanes. Concentration in vacuo afforded 20.01 g of 2-Chloromethyl-3-(tri-O-benzyl-α-L-C-fucopyranoside)-1-propene (1) (85%).

Example 2

Preparation of 2-(Tri-O-benzyl-α-L-C-methylfucopyranose)-3-[3-O-(betulinic acid)]-1-propene (2)

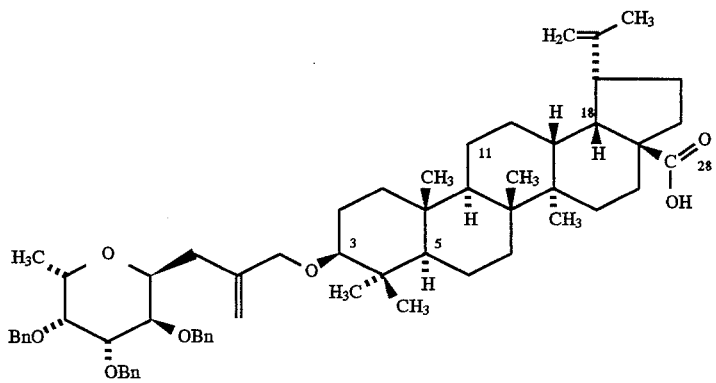

To a solution of sodium hydride (126 mg, 5.25 mmole, 6.00 mmole equiv.) in anhydrous 25% dimethylformamide in tetrahydrofuran (5.5 mL) at ambient temperature was added betulinic acid (0.40 g, 0.876 mmol, 1.00 mmole equiv.) in a minimum amount of anhydrous 25% dimethylformamide in tetrahydrofuran. Sodium iodide (1.31 g, 8.76 mmole, 10.00 mmole equv.) and Tetra-n-butylammonium Iodide (32.4 mg, 0.0876 mmole, 0.10 mmole equiv.) were added and the reaction contents were warmed to a gentle reflux (until the evolution of $H_2$ ceased) for 30 minutes. 2-Chloromethyl-3-(tri-O-benzyl-α-L-C-fucopyranoside)-1-propene (1) (1.0 g, 1.97 mmole, 2.30 mmole equiv.) was added dropwise in anhydrous 25% dimethylformamide in tetrahydrofuran (5.5 mL, total of 0.08M) and gently refluxed for 6 hours. After 6 hours at reflux, the reaction was terminated by the careful addition of 50% methanol in toluene (2 mL) at 0° C. and then 4M hydrochloric acid until the pH was 1–2 and then diluted with ethyl acetate. The heterogeneous layers were separated and the organic phase was washed with portions of 1.0M hydrochloric acid, sodium bicarbonate and brine. The crude product was dried over anhydrous sodium sulfate, filtered and plugged through a small pad of silica gel eluting with ethyl acetate. The solvent was removed in vacuo which afforded an oil that was chromatographed on Baker grade flash silica gel (47–61 mm) (ratio 50 to 1) and eluted with benzene, 10% ethyl acetate in hexane, 30% ethyl acetate in hexane, 50% ethyl acetate in hexane and finally with 5% methanol in chloroform. Concentration in vacuo afforded 0.440 g of 2-(tri-O-benzyl-α-L-C-methylfucopyranose)-3-[3-O-(betulinic acid)]-1-propene (2) (67%) as a white foam powder.

and then 4M hydrochloric acid until the pH is 1–2 and the reaction contents are diluted with ethyl acetate. The heterogeneous layers are separated and the organic phase is washed twice with portions of 1.0M hydrochloric acid, saturated sodium thiosulfite and brine. The crude product is dried over anhydrous sodium sulfate, filtered and plugged through a small pad of silica gel and eluted with ethyl acetate. The solvent is removed in vacuo which afforded an oil that is chromatographed on Baker grade flash silica gel (47–61 mm) (ratio 50 to 1) and eluted with 10% ethyl acetate in hexane, 50% ethyl acetate in hexane, 100% ethyl acetate. Concentration in vacuo afforded 2-(tri-O-benzyl-α-L-C-methylfucopyranose)-3-[3-O-(betulinic acid)]-1-propene (2) as a white foam powder.

Example 3

Preparation of 1-[3-O-(betulinic acid)]-2-(α-L-C-methylfucopyranose)-propane (3)

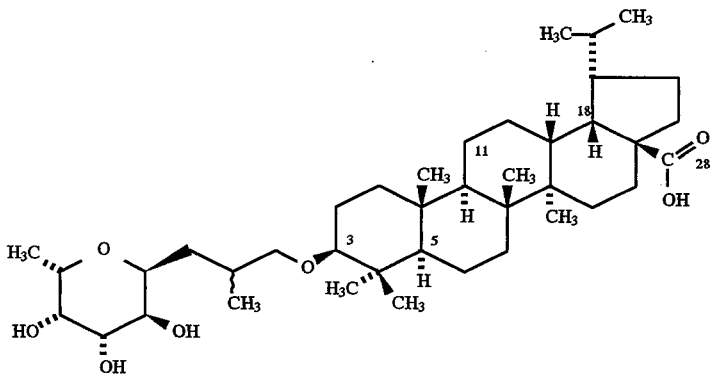

Alternate Procedure 2-(Tri-O-benzyl-α-L-C-methylfucopyranose)-3-[3-O-(betulinic acid)]-1-propene (2) may also be prepared by the following procedure.

To a solution of sodium hydride (126 mg, 5.25 mmole, 6.00 mmole equiv.) in anhydrous benzene (5.5 mL) at ambient temperature is added betulinic acid (0.40 g, 0.876 mmol, 1.00. mmole equiv.) dropwise in a minimum amount of anhydrous tetrahydrofuran. Sodium iodide (1.31 g, 8.76 mmole, 10.00 mmole equv.) and Tetra-n-butylammonium Iodide (32.4 mg, 0.0876 mmole, 0.10 mmole equiv.) are added and the reaction contents are warmed to a gentle reflux (until the evolution of $H_2$ ceased) for 30 minutes. 2-Chloromethyl-3-(tri-O-benzyl-α-L-C-fucopyranoside)-1-propene (1) (1.0 g, 1.97 mmole, 2.30 mmole equiv.) is added dropwise in anhydrous tetrahydrofuran (5.5 mL, total reaction concentration of 0.08M) and gently refluxed for 6 hours. After 6 hours at reflux, the reaction is terminated by the careful addition of 50% methanol in toluene (2 mL) at 0° C.

A solution of 2-(tri-O-benzyl-α-L-C-methylfucopyranose)-3-[3-O-(betulinic acid)]-1-propene (2) (300 mg, 0.323 mmole, 1.00 mmole equiv.) in 10% acetic acid in methanol (ethyl acetate can be added to enhance solubility) (1.6 mL), was added to 10% palladium on carbon (35 mg per mmole of substrate) and placed on a parr hydrogenation apparatus. The reaction vessel was evacuated and re-filled with hydrogen thrice and then shaken at 50 PSI for 48 hours. The reaction was terminated by filtering the contents through Celite to remove the catalyst. The reaction mixture was concentrated in vacuo and washed with dichloromethane to give a white powder to afforded 131.7 mg of 1-[3-O-(betulinic acid)]-2-(α-L-C-methylfucopyranose)-propane (3) (62%).

Example 4

Preparation of 1-[3-O-(Betulinic acid-27,29-diol)]-2-(tri-O-benzyl-α-L-C-methylfucopyranose)-2',3'-propanediol (4)

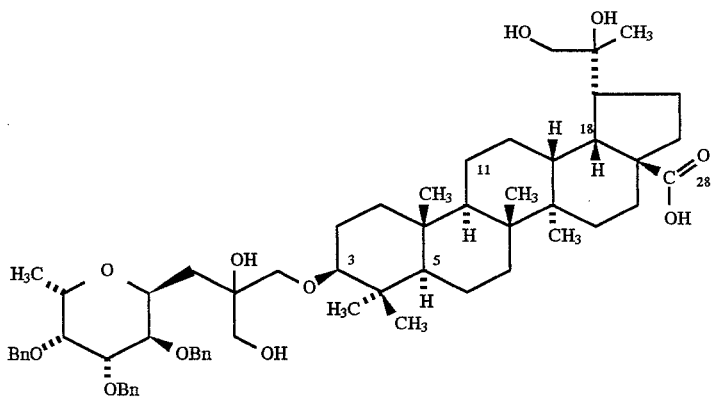

To a solution of 2-(tri-O-benzyl-α-L-C-methylfucopyranose)-3-[3-O-(betulinic acid)]-1-propene (2) (1.00 g, 1.06 mmole, 1.00 mmole equiv.) in anhydrous dichloromethane (5.3 mL, 0.2M) at ambient temperature is added osmium tetroxide (0.0106 mmole, 21.2 mL of a 0.5M solution in toluene, 0.01 mmole equiv.) and N-methylmorpholine-N-oxide (1.24 g, 10.6 mmole, 10.00 mmole eqiv.). The reaction contents are stirred at ambient temperature for 6 days and the reaction is terminated by the addition of 25% aqueous sodium metasulfite and stirred for 1 hour. The heterogeneous layers are separated and the organic phase is washed twice with portions of 25% aqueous sodium metasulfite, 1.0M hydrochloric acid, sodium bicarbonate and brine. The crude product is dried over anhydrous sodium sulfate, filtered and plugged through a small pad of silica gel with ethyl acetate. The solvent is removed in vacuo which affords an oil that is chromatographed on Baker grade flash silica gel (47–61 mm) (ration of 50 to 1) and eluted with 50% ethyl acetate in hexane and then 5% methanol in chloroform. Concentration in vacuo affords 1-[3-O-(betulinic acid-27,29-diol)]-2-(tri-O-benzyl-α-L-C-methylfucopyranose)-2',3'-propanediol (4).

Example 5

Preparation of 1-[3-O-(Betulinic acid-27,29-diol)]-2-(α-L-C-methyl-fucopyranose)-2', 3'-propanediol (5)

A solution of 1-[3-O-(betulinic acid-27,29-diol)]-2-(tri-O-benzyl-α-L-C-methylfucopyranose)-2',3'-propanediol (4) (2.00 g, 2.02 mmole, 1.00 mmole equiv.) in 10% acetic acid in methanol (10 mL, 0.2M), was added to 10% palladium on carbon (35 mg per mmole of substrate wetted with toluene) and the contents placed on a parr hydrogenation apparatus. The reaction vessel is evacuated and re-filled with hydrogen thrice and then shaken at 50 PSI for 48 hours. The reaction is terminated by filtering the contents through Celite to remove the catalyst. Concentration in vacuo affords a white powder which is filtered and rinsed with dichloromethane to give 1-[3-O-(betulinic acid-27,29-diol)]-2-(α-L-C-methylfucopyranose)-2',3'-propanediol (5).

A further manipulation of a glycerol linking arm is necessary to give a 3'-O-glycosylated derivative. This can be accomplished by using the partial protection method developed by Garegg and Hultberg [Garegg, P. J., Hultberg, H., Carbo. Res. 93 (1981) C10–C11.] involving reductive ring opening of a 2',3'-benzylidene acetal with sodium cyanoborohydride in THF.

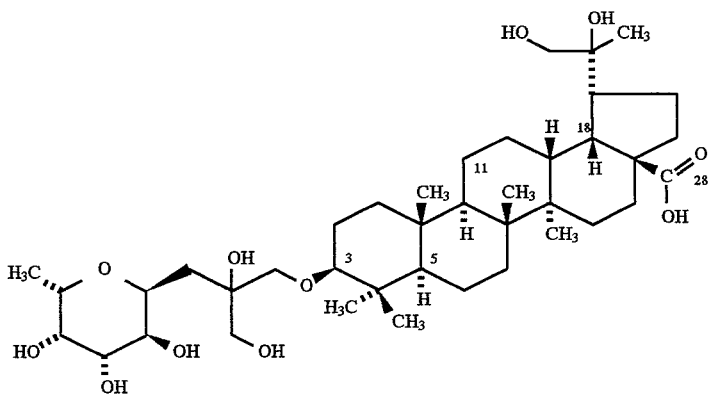

Example 6

Preparation of 1-[3-O-(27-Oxo-betulinic acid)]-2-(α-L-C-methylfucopyranose)-2'-oxo-ethane tri-sulfate (6)

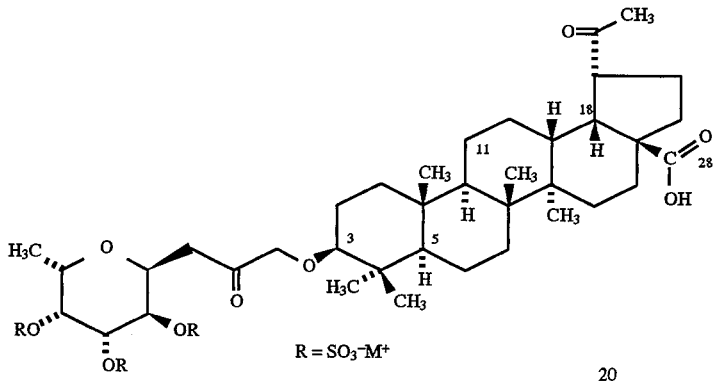

To a solution of 1-[3-O-(27-oxo-betulinic acid)]-2-(α-L-C-methylfucopyranose)-2'-oxo-ethane (8) (50 mg, 75.8 mmole, 1.00 mmole equiv.) in anhydrous dimethylformamide (3.5 mL, 0.2M) at ambient temperature is added sulfur trioxide pyridine complex (758 mmole, 10 mmole equiv.) polymer. Graf, W. *Chem. Ind.* 232 (1987). The reaction contents are stirred at ambient temperature and then warmed to a gentle reflux for 8 hours. The reaction is terminated by cooling to ambient temperature, neutralization with excess NaHCO$_3$ and filtering the polymer through celite. The solvent is removed in vacuo which affords an oil that is azeotrophed with toluene. Concentration in vacuo affords 1-[3-O-(27-oxo-betulinic acid)]-2-(α-L-C-methylfucopyranose)-2'-oxo-ethane trisulfate (6).

Example 7

Preparation of 1-[3-O-(27-Oxo-betulinic acid)]-2-(tri-O-benzyl-α-L-C-methylfucopyranose)-2'-oxo-ethane (7)

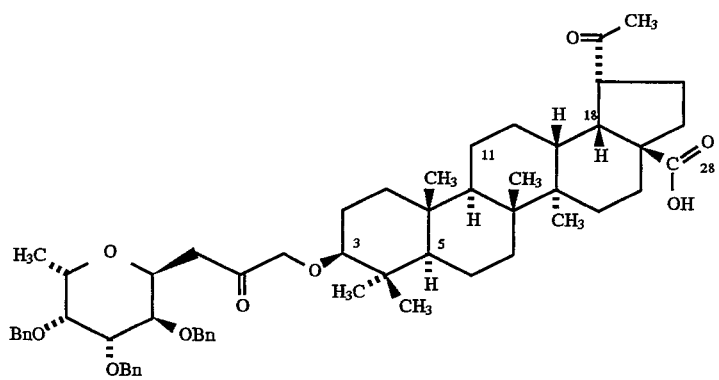

1-[3-O-(27-oxo-betulinic acid)]-2-(α-L-C-methylfucopyranose)-2'-oxo-ethane tri-sulfate (6).

Alternate Procedure

1-[3-O-(27-Oxo-betulinic acid)]-2-(α-L-C-methylfucopyranose)-2'-oxo-ethane tri-sulfate (6) may also be prepared by the following procedure To a solution of 1-[3-O-(27-oxo-betulinic acid)]-2-(α-L-C-methylfucopyranose)-2'-oxo-ethane (8) (50 mg, 75.8 mmole, 1.00 mmole equiv.) in anhydrous dimethylformamide (3.5 mL, 0.2M) at ambient temperature is added sulfur trioxide pyridine complex (758 mmole, 10 mmole equiv.). The reaction contents are stirred at ambient temperature and then warmed to a gentle reflux for 8 hours. The reaction is terminated by cooling to ambient temperature, neutralization with excess NaHCO$_3$ and filtering through celite. The solvent is removed in vacuo which affords an oil that is azeotrophed with toluene. Concentration in vacuo affords 1-[3-O-(27-oxo-betulinic acid)]-2-(α-L-C-methylfucopyranose)-2'-oxo-ethane trisulfate (6).

To a solution of 2-(tri-O-benzyl-α-L-C-methylfucopyranose)-3-[3-O-(betulinic acid)]-1-propene (2) (40 mg, 0.043 mmole, 1.00 mmole equiv.) in anhydrous dichloromethane (0.210 mL, 0.2M) at -78° C. is added excess ozone. The reaction contents are stirred at -78° C. for 1 hour and the reaction is terminated by the addition of dimethylsulfide (26.9 mg, 31.7 mL, 0.431 mmole, 10.00 mmole equiv.) and stirred for 1 hour and allowed to warm to ambient temperature. Water is added and the heterogeneous layers are separated and the organic phase is washed twice with portions of 1.0M hydrochloric acid, sodium bicarbonate and brine. The crude product is dried over anhydrous sodium sulfate, filtered and plugged through a small pad of silica gel of a weight ratio of 10:1. The solvent is removed in vacuo which affords an oil that is chromatographed on Baker grade flash silica gel (47–61 mm) (ratio of 50 to 1) and eluted with 50% ethyl acetate in hexane.

Concentration in vacuo affords 1-[3-O-(27-oxo-betulinic acid)]-2-(tri-O-benzyl-α-L-C-methylfucopyranose)-2'-oxo-ethane (7).

Example 8

Preparation of 1-[3-O-(27-Oxo-betulinic acid)]-2-(α-L-C-methylfucopyranose)-2'-oxo-ethane (8)

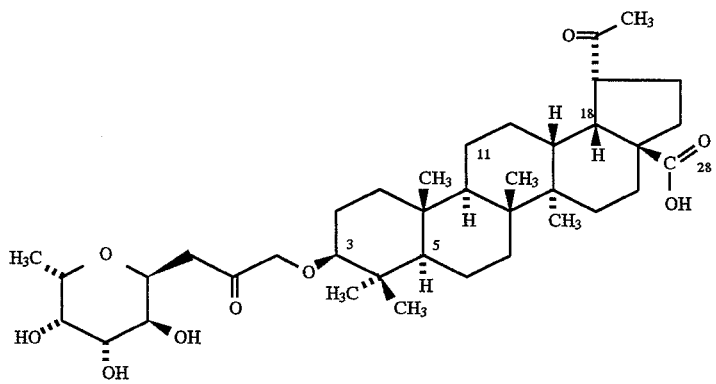

A solution of 1-[3-O-(betulinic acid)]-2-oxo-2-(tri-O-benzyl-α-L-C-methylfucopyranose)-ethane (7) (15 mg, 0.0159 mmole, 1.00 mmole equiv.) in 10% acetic acid in methanol (ethyl acetate can be added to enhance solubility) (1.5 mL), is added to 5% palladium on carbon (35 mg per mmole of substrate) and placed on a parr hydrogenation apparatus. The reaction vessel is evacuated and re-filled with hydrogen thrice and then shaken at 50 PSI for 48 hours. The reaction is terminated by filtering the contents through Celite to remove the catalyst. The reaction mixture is concentrated in vacuo and washed with dichloromethane to give 1-[3-O-(27-oxo-betulinic acid)]-2-(α-L-C-methylfucopyranose)-2'-oxo-ethane (8).

Example 9

Anti-inflammatory Effects

Using the arachidonic acid (AA), murine skin inflammation model, described by Harris, R. R. et al. (Skin Pharmacol 3: 29–40 (1990)) the anti-inflammatory activity of 1-[3-O-(betulinic acid)]-2-(α-L-C-methylfucopyranose) propane (3) was tested. For comparison, betulinic acid was also tested. All compounds were dissolved at 50 mg/mL in CHCl$_3$:CH$_3$OH (1:1) and 10 mL of each compound was applied two times to the ear, at about a 2 minute interval or the period of time it took for the solvent to evaporate from the ear, immediately following arachidonic acid (AA). A control of AA alone was run. Ninety minutes later a 6 mm disk of each ear was removed and weighed. In three separate experiments, as shown in Table 1, it was observed that the percent inhibition of swelling caused by AA alone was reduced by about 36.7%, 46.6%, and 59% for the 1-[3-O-(betulinic acid)]-2-(α-L-C-methylfucopyranose)-propane (3) and 0%, 12.2%, and 25.9% for betulinic acid.

These results clearly establish that the betulinic acid derivatives of the invention have medical utility for the treatment of inflammation. In all three experiments the betulinic acid derivative inhibited the inflammatory response. Moreover, it should be noted that these effects were observed at a lower concentration, 1.5 μmoles, than the effects observed for betulinic acid which was used at 2.2 μmoles.

TABLE 1

Anti-Inflammatory Activities
Topical Administration in Arachidonic Acid Ear Model.

| Compound | % Inhibition of Swelling | Amount Applied in mg (mmoles) |
|---|---|---|
| Betulinic acid | 0.0%, 12.2%, 25.9% | 1 mg (2.2 mmoles) |
| Compound (3) | 36.7%, 46.6%, 59% | 1 mg (1.5 mmoles) |

Example 10

Inhibition of Leukotriene Biosynthetic Enzymes

Several assays can be performed to assess the inhibitory activity of the invention compounds against enzymes involved in leukotriene biosynthesis. Assays for 5-lipoxygenase are known in the art and can be readily performed as described by Shimuzu, T., et al., Proc. Natl. Acad. Sci. USA 81: 693–698, (1984) and Epan, R., et al., J. Biol. Chem. 260: 11554–11559 (1985).

The compounds of the instant invention were assayed for their capacity to inhibit 5-lipoxygenase as now described using a crude enzyme preparation from rat basophilic leukemia cells (RBL-1) (Shimuzu, T., Radmark, O. and Samuelsson, B. Proc. Natl. Acad. Sci. USA 81: 698–693 (1984) and Egan, R. W. and Gale, P. H. J. Biol. Chem. 260: 11554–11559) (1985).

Test compounds are pre-incubated with the enzyme for 5 minutes at room temperature and the reaction is initiated by addition of substrate, linoleic acid. Following an 8 minute incubation at room temperature, the reaction is terminated by addition of NaOH, and absorbance read at 234 nm to determine levels of 5-HETE. Compounds are screened at 50 μM.

Example 11

Anti-Metastatic Activity

Figure 4:
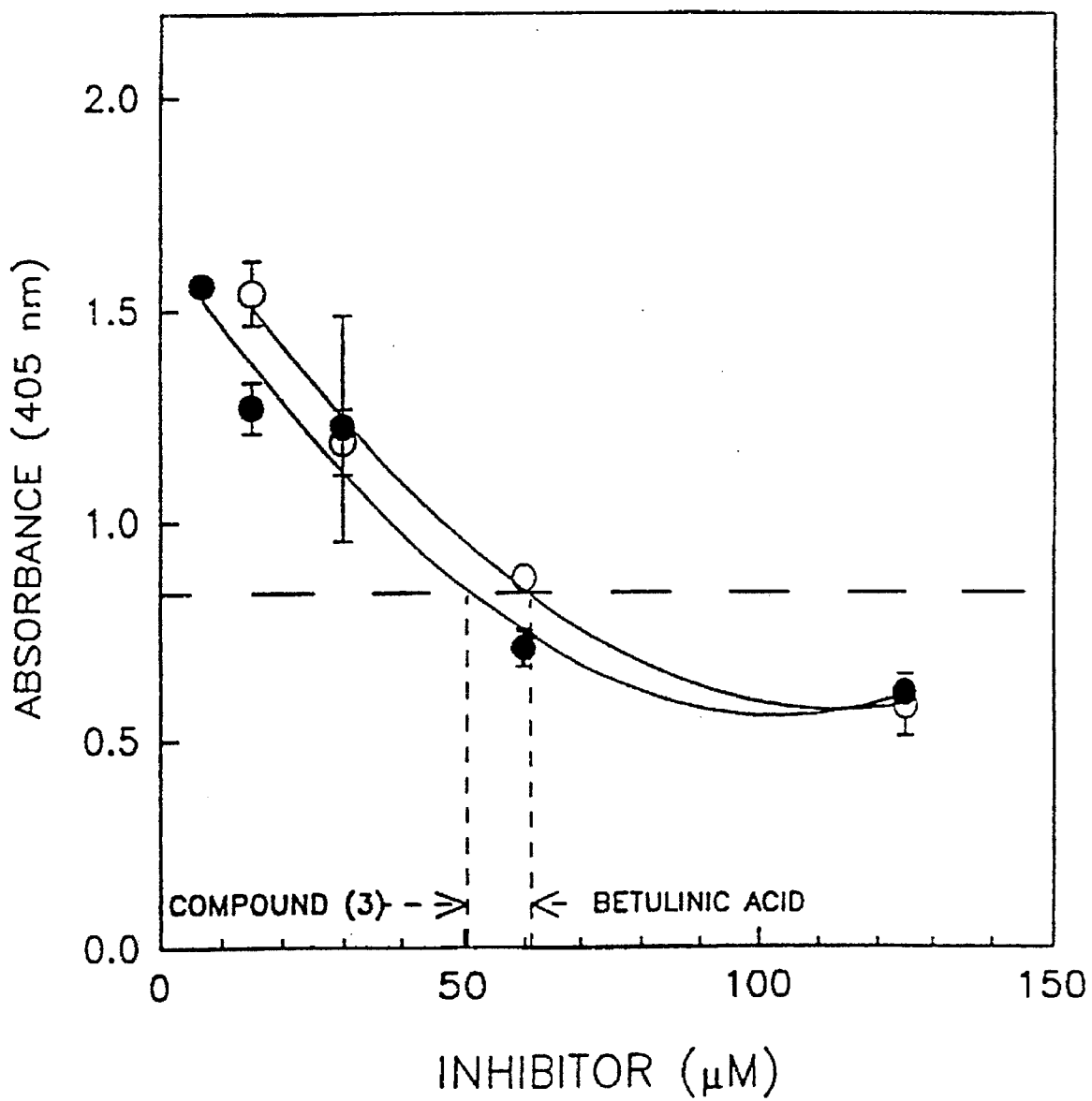
FIG. 4 shows the inhibition of cancer cell adhesion to E-selectin by compound (3) and betulinic acid. The results shown in this figure are from a different experiment than the results shown in FIG. 3.

Experiments were conducted to determine the capacity of the invention compounds to interfere with the binding of cancer cells to E-selectin. The compounds are dissolved in dimethylformamide (DMF) prior to being assayed. The assay consists of combining the appropriate test compound, E-selectin chimera which contains an IgG tail, a detection system consisting of biotinylated anti-human Ig (Fc specific), and streptavidin-alkaline phosphatase all in 10 mM Tris, 150 mM NaCl, pH 7.2–7.4, plus 1 mM $Ca^{++}$. The mixture is rotated briskly on a rotary platform at room temperature for 30–60 minutes. Particulate matter is removed by centrifugation, and the soluble fraction is transferred onto 96-well microtiter plates containing glutaraldehyde fixed LS174T colon carcinoma cells. After 60 minutes at 37° C., plates are washed and E-selectin chimera bound to cells is quantified by addition of pNPP substrate in 1M diethanolamine buffer containing 0.1 mg/ml $MgCl_2$ at pH 9.8. Plates are developed in the dark and read at 405 nm. The $IC_{50}$ values are the lowest concentrations from serial two-fold dilutions (quadruplicate wells at each concentration) which inhibits by 50% or more relative to the control. DMF (vehicle) typically has no effect. It will be appreciated that both betulinic acid and compound (3) significantly interfere with cancer cell binding to E-selectin binding. The results from two experiments are shown in FIGS. 3 and 4. The $IC_{50}$ values for compound (3) (30 μm) are lower than for betulinic acid (60 μm). These findings support the suitability of compound (3) for the treatment or prevention of certain forms of metastatic cancers. Moreover, these findings further stress the enhanced multi-medicament activities of the invention compounds.

Example 12

Inhibition of P-Selectin Binding

Certain of the invention compounds were tested for their capacity to inhibit P-selectin binding to HL-60 cells, and to a chemical known to bind to P-selectin, 2,3 sLex. The following materials and procedures were used.

Compound Preparation

Compound (3) of Example 3 and betulinic acid were solubilized in DMF to yield 100 mM solutions.

P-Selectin Detection Solutions. Goat F(ab')2 anti-human IgG (Fc spec.)-biotin and streptavidin-AP were diluted 1:1000 in 1% BSA-TBS with 1 mM $Ca^{++}$. An Elisa assay was utilized to measure P-selectin binding to 2,3 sLex, and P-selectin was added at 300 ng/ml. An Elisa assay was also used to assay for the capacity of the invention compounds to inhibit HL-60 cell binding to P-selectin. HL-60 cells were used, and P-selectin was added at 200 ng/ml.

Plate Preparation 2,3 sLex was coated at 30 pmoles/well to Probind microtiter plates for Elisa. The glycolipid was added at 50 μl/well in 50% MeOH and allowed to evaporate overnight. Elisa plates and HL-60 assay plates were blocked with 5% BSA-TBS $Ca^{++}$ for more than an hour at room temperature. The plates were washed with TBS without $Ca^{++}$.

Cell Preparation

HL-60 cells were harvested by centrifugation, washed with TBS no $Ca^{++}$, counted, and the density adjusted to $2 \times 10^6$/ml in 1% BSA-TBS $Ca^{++}$.

Assay

Figure 5:
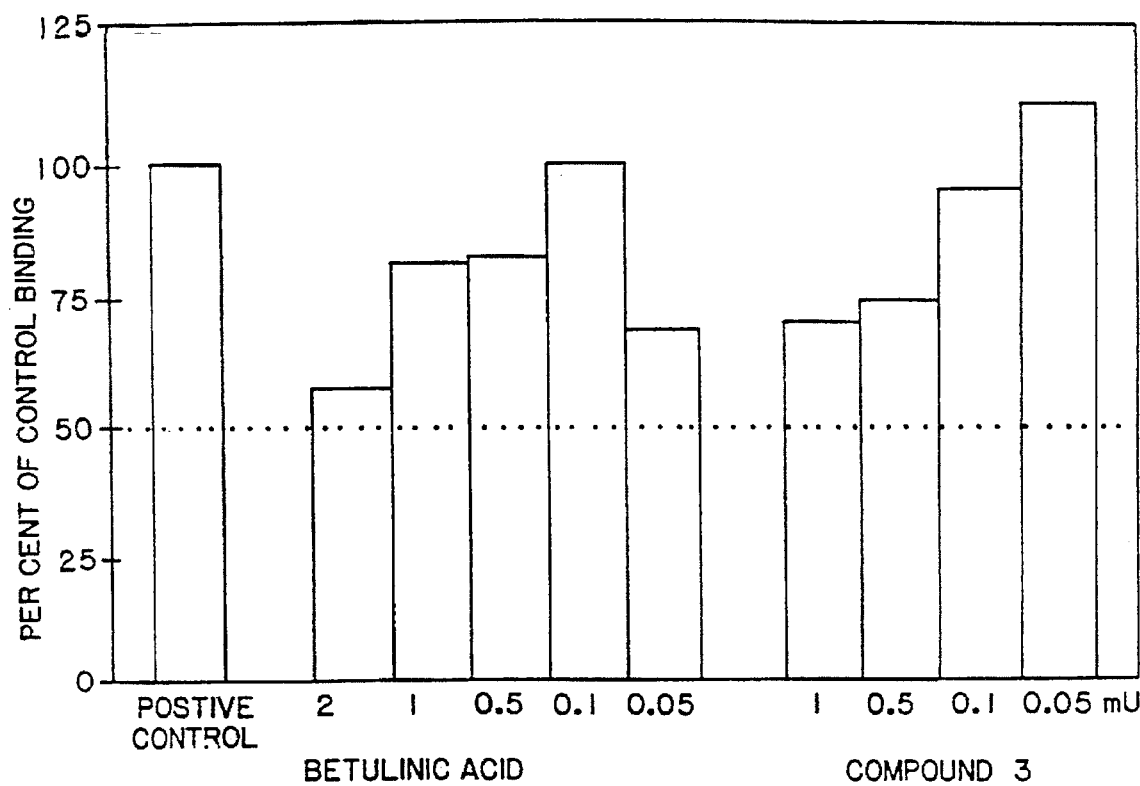
FIG. 5 shows the inhibitory effects of compound (3) on P-selectin binding to sLex.

Briefly, the assays were conducted as follows. Compound (3) and betulinic acid were added to P-selectin detection solutions at 4, 2, 1, 0.5, 0.25 and 0.125 mM for the HL-60 based assay, and at 2, 1, 0.5, 0.25, 0.125 and 0.063 mM for the assay involving 2,3 sLex. DMF solutions were added directly to 1% BSA/TBS-Ca for dilutions through 0.5 mM. Lower concentrations were made in serial two-fold dilutions in BSA-TBS. These solutions were incubated at room temperature on a rotating platform for 1 hour, centrifuged to pellet particulate matter, and then added in triplicate for 2,3 sLex coated plates, or quadruplicate for HL-60 cells at 50 μl/well. An equal volume of HL-60 cells was added to wells for the cell based assay. The 2,3 sLex coated plates were incubated at 37° C. for 45 minutes, washed 3× with TBS, and 50 μl of substrate added to each well. Plates with HL-60 cells were incubated at 4° C. for 1 hour, the cells pelleted by centrifugation and washed 3× with TBS. For both assays, substrate was added at 75 μl/well. After color developed to an appropriate intensity, 50 μl/well was transferred to another plate for O.D. determination at 405 nm. FIG. 5 shows the results. Compound (3) did inhibit P-selectin binding to sLex, and it was somewhat more effective than betulinic acid.

The results established that the $IC_{50}$ for inhibiting P-selectin binding to 2,3 sLex for betulinic acid was about 125 μM; for compound (3) it was <1 and >0.5 mM. The HL-60 assay showed that betulinic acid interfered with P-selectin binding to HL-60 cells in a dose dependent way. The $IC_{50}$ was about 0.75 mM. Compound (3) also interfered with P-selecting binding to HL-60 cells in a dose dependent manner, but was again less effective than betulinic acid. The $IC_{50}$ was about 2 mM.

These results confirm and extend those presented in Examples 9–11 in that the invention compounds have a marked and significant multi-medicament capacity, and can interfere with selectin binding generally, as shown here relating to P-selectin, and in Example 11 to E-selectin. Importantly, the invention compounds interfere with the binding of human HL-60 cells to both P-selectin and E-selectin.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

What is claimed is:

1. A compound comprising the following structural formula (I):

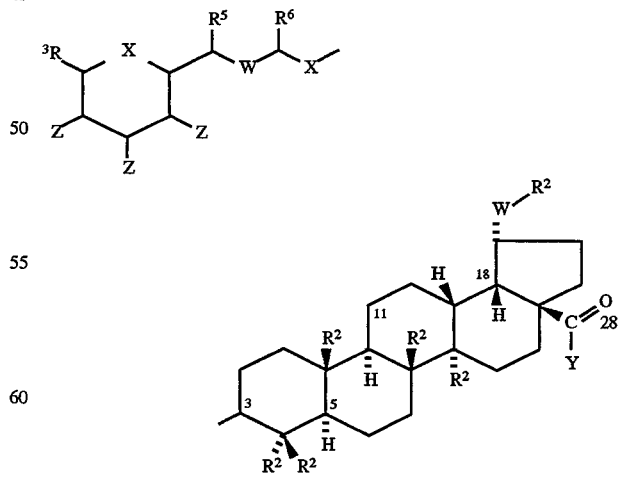

wherein:

Y is $OR^1$, $NR^1_2$ or $O-M^1$;

$R^1$ is H or lower alkyl:

$M^1$ is $Na^+$, $K^+$, $Mg^{++}$, or $Ca^{++}$ ions;

each $R^2$ is independently $CH_2OR^1$ or $CH_3$;

each $R^3$ is independently H, $CH_3$, lower alkyl, COY, $CH_2OH$, $CH_2OCH_2CH=CH_2$, or $CH_2OSO_3$-$M^1$;

each Z is independently $NHR^1_2$, $NR^1Ac$, $NR^1Bz$, H, $OCH_3$, lower alkyl, OH, $OSO_3$-$M^1$, $OCH_2CH=CH_2$, $OCH_2CO_2H$ or O-glycoside;

each X is independently O, S, $NR^1$ or $NR^1_2$;

each W is independently C=O, C=$CR^1_2$, $CR^1CR^1_3$, $CR^1CR^1_2OR^1$, $COR^1$-$CR^1OR^1$, $COR^1CR^1_2OR^1$, $CR^1CR^1_2NR^1_2$, $CR^1CR^1_2OCR^1COY$ or $CHR^4$;

$R^4$ is H, OH, $OSO_3$-$M^1$, $NH(CH_2)_nNH_2$, where n=1–8, or $NH$-Ph-$NH_2$ where Ph is a phenyl or naphthyl ring substituted with up to 3 amine functionalities and the remaining substitutions can be H, $R^1$, $R^2$, or COY; and $R^5$ and $R^6$ are independently H, $CH_3$ or taken together form a 5 or 6 membered carbocyclic ring.

2. The compound as described in claim 1, wherein $R^1$ is hydrogen; $R^2$ and $R^3$ are $CH_3$; $R^5$ and $R^6$ are hydrogen; X is oxygen; and W is $CHCH_3$.

3. The compound as described in claim 1, wherein $R^1$ is hydrogen; $R^2$ and $R^3$ are $CH_3$; $R^5$ and $R^6$ are hydrogen; X is oxygen; and W is $C(OH)CH_2OH$.

4. The compound

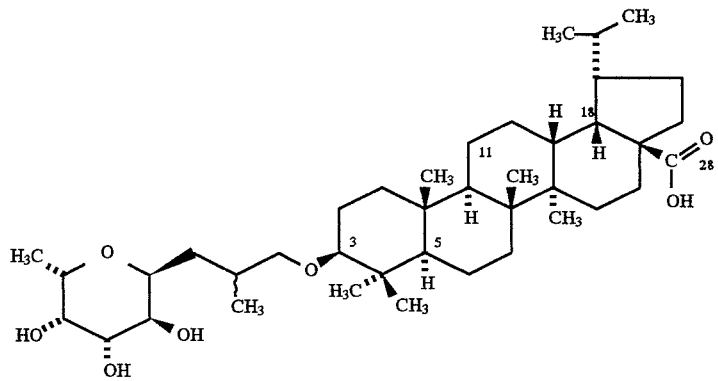

5. The compound

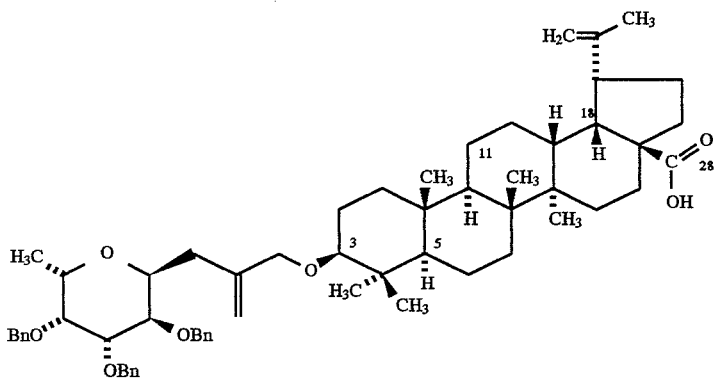

6. The compound

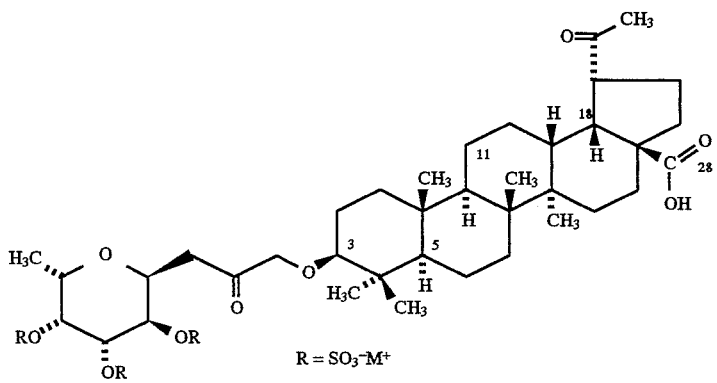

7. The compound

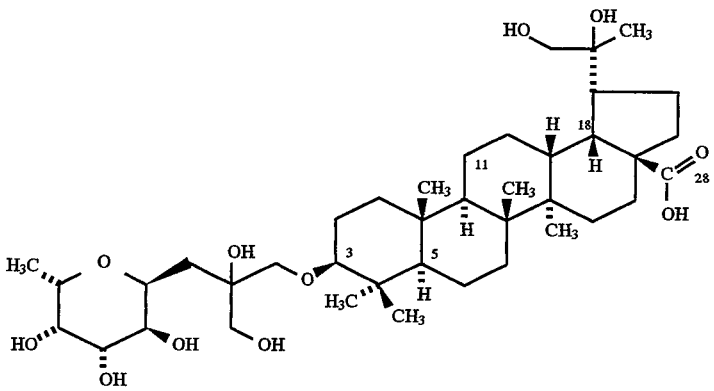

8. A pharmaceutical composition, comprising:

a pharmaceutically acceptable excipient carrier; and a therapeutically effective amount of a compound comprising the following general structural formula (I).

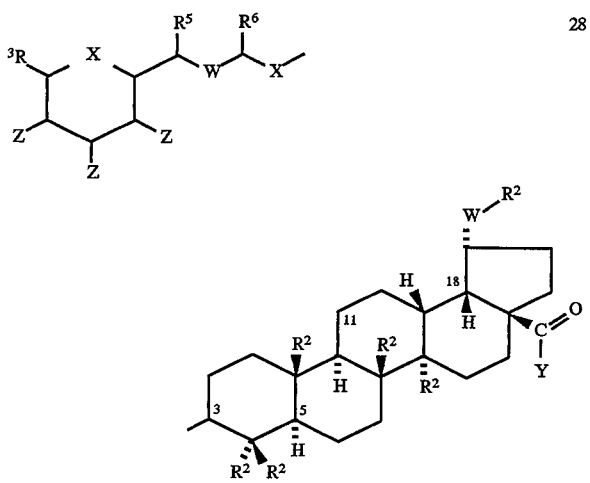

wherein:

Y is $OR^1$, $NR^1_2$ or $O-M^1$;

$R^1$ is H or lower alkyl;

$M^1$ is $Na^+$, $K^+$, $Mg^{++}$, or $Ca^{++}$ ions;

each $R^2$ is independently $CH_2OR^1$ or $CH_3$;

each $R^3$ is independently H, $CH_3$, lower alkyl, COY, $CH_2OH$, $CH_2OCH_2CH=CH_2$, or $CH_2OSO_3-M^1$;

each Z is independently $NHR^1_2$, $NR^1Ac$, $NR^1Bz$, H, $OCH_3$, lower alkyl, OH, $OSO_3-M^1$, $OCH_2CH=CH_2$, $OCH_2CO_2H$ or O-glycoside;

each X is independently O, S, $NR^1$ or $NR^1_2$;

each W is independently C=O, C=$CR^1_2$, $CR^1CR^1_3$, $CR^1CR^1_2OR^1$, $COR^1$-$CR^1OR^1$, $COR^1CR^1_2OR^1$, $CR^1CR^1_2NR^1_2$, $CR^1CR^1_2OCR^1COY$ or $CHR^4$;

$R^4$ is H, OH, $OSO_3-M^1$, $NH(CH_2)_nNH_2$, where n=1–8, or $NH-Ph-NH_2$ where Ph is a phenyl or naphthyl ring substituted with up to 3 amine functionalities and the remaining substitutions can be H, $R^1$, $R^2$, or COY; and $R^5$ and $R^6$ are independently H, $CH_3$ or taken together form a 5 or 6 membered carbocyclic ring.

9. The pharmaceutical composition as described in claim 8, wherein $R^1$ is hydrogen; $R^2$ is $CH_3$; $R^5$ and $R^6$ are hydrogen; X is oxygen; and W is $CHCH_3$.

10. The pharmaceutical composition as described in claim 8, wherein $R^1$ is hydrogen; $R^2$ is $CH_3$; $R^5$ and $R^6$ are hydrogen; X is oxygen; and W is $C(OH)CH_2OH$.

11. A method of treating inflammation, comprising the step of:

administering to a patient in need thereof a therapeutically effective amount of the pharmaceutical composition of claim 8.

12. A method as in claim 11 wherein the pharmaceutical composition of claim 9 is administered to the patient with a pharmaceutically acceptable excipient carrier.

13. A method as in claim 11 wherein the compound of claim 4 is administered to the patient with a pharmaceutically acceptable carrier.

14. A method of determining a site of inflammation in a patient, comprising the steps of:

administering to the patient the compound of claim 1, wherein the compound of claim 1 has a detectable label attached to it;

allowing the labelled compound sufficient time to circulate in the patient; and detecting the location of the labelled compound in the patient, whereby the site of inflammation is determined.

15. The method as described in claim 14, wherein the label is a radioactive label.

16. A compound, comprising:

a triterpenoid having a 3 position;

a glycoside; and a three carbon linker moiety, wherein the three carbon linker moiety binds the glycoside to the 3 position of the triterpenoid.

17. A compound as in claim 16 wherein the glycoside is fucose.

18. A method of producing a compound, comprising:

binding a glycoside to a triterpenoid, wherein the glycoside is bound to the 3 position of the triterpenoid by a three carbon linker moiety.

19. A method as in claim 18, wherein the glycoside is fucose.

* * * * *